(12) United States Patent
Nishigishi (10) Patent No.: US 10,383,645 B2
(45) Date of Patent: Aug. 20, 2019

(54) CATHETER

(71) Applicant: ASAHI INTECC CO., LTD., Seto-shi, Aichi (JP)

(72) Inventor: Makoto Nishigishi, Owariasahi (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 211 days.

(21) Appl. No.: 15/208,909

(22) Filed: Jul. 13, 2016

(65) Prior Publication Data

US 2017/0105742 A1  Apr. 20, 2017

(30) Foreign Application Priority Data

Oct. 20, 2015 (JP) ................................. 2015-206219

(51) Int. Cl.
*A61B 17/221* (2006.01)
*A61B 17/22* (2006.01)
*A61B 17/3207* (2006.01)

(52) U.S. Cl.
CPC .... *A61B 17/221* (2013.01); *A61B 17/320725* (2013.01); *A61B 2017/22001* (2013.01); *A61B 2017/2212* (2013.01); *A61B 2017/2215* (2013.01); *A61B 2017/22072* (2013.01)

(58) Field of Classification Search
CPC .......... A61B 17/221; A61B 17/320725; A61B 2017/22001; A61B 2017/22072; A61B 2017/2212; A61B 2017/2215; A61F 2/01; A61F 2/013; A61F 2/90; A61M 25/04; A61M 29/02
USPC ......................................... 606/108, 191–200
See application file for complete search history.

(56) References Cited

U.S. PATENT DOCUMENTS

| 5,180,368 A | 1/1993 | Garrison |
| 5,836,868 A | 11/1998 | Ressemann et al. |
| 5,897,567 A | 4/1999 | Ressemann et al. |
| 8,333,783 B2 | 12/2012 | Braun et al. |
| 8,574,258 B2 | 11/2013 | Braun et al. |
| 8,672,990 B2 | 3/2014 | Holman et al. |

(Continued)

FOREIGN PATENT DOCUMENTS

| EP | 0719111 A1 | 7/1996 |
| EP | 0794734 A1 | 9/1997 |

(Continued)

OTHER PUBLICATIONS

Feb. 20, 2017 Search Report issued in European Patent Application No. 16178937.5.

(Continued)

*Primary Examiner* — Kathleen S Holwerda
(74) *Attorney, Agent, or Firm* — Oliff PLC (57) ABSTRACT

A catheter includes a protective film covering an inner periphery of a proximal end side of a tubular mesh member, the tubular mesh member being expandable and contractible in a radial direction. The tubular mesh member including a first wire that is interwoven with a second wire. The protective film being joined only to any one of either the first wire or the second wire. The catheter has improved efficiency for removing a blockage in a blood vessel, and the catheter can prevent breakage of a retrograde guide wire. Additionally, the mesh member having the protective film is able to smoothly expand and contract.

10 Claims, 7 Drawing Sheets

(56) References Cited

U.S. PATENT DOCUMENTS

| | | | |
|---|---|---|---|
| 2002/0091409 A1 | 7/2002 | Sutton et al. | |
| 2004/0260333 A1* | 12/2004 | Dubrul | A61B 17/22 606/200 |
| 2005/0033311 A1* | 2/2005 | Guldfeldt | A61M 25/04 606/108 |
| 2007/0225750 A1 | 9/2007 | Ren et al. | |
| 2011/0264132 A1* | 10/2011 | Strauss | A61B 17/12022 606/194 |
| 2015/0005810 A1* | 1/2015 | Center | A61F 2/01 606/200 |

FOREIGN PATENT DOCUMENTS

| | | |
|---|---|---|
| EP | 1898846 | 7/2006 |
| JP | 3655920 B2 | 6/2005 |
| JP | 2008-541835 A | 11/2008 |
| JP | 2011-516183 A | 5/2011 |
| JP | 2011-517424 A | 6/2011 |
| WO | 94/24946 A1 | 11/1994 |
| WO | 2009/124288 A1 | 10/2009 |

OTHER PUBLICATIONS

Apr. 9, 2018 Office Action issued in Japanese Application No. 2015-206219.

Sep. 27, 2018 Office Action issued in Chinese Patent Application No. 201610265128.X.

* cited by examiner

CATHETER

CROSS REFERENCE TO RELATED APPLICATION

This application claims priority to Japanese Patent Application No. 2015-206219 filed in the Japan Patent Office on Oct. 20, 2015, the entire content of which is incorporated by reference.

BACKGROUND

The occlusion of a blood vessel, such as chronic total occlusion (CTO), may occur due to a blockage in the blood vessel. Medical devices used for treating such an occlusion include, for example, a catheter that removes a blockage in a vessel. Patent Document 1 discloses a traditional catheter that includes a blockage-removing element in which two or more wires are interwoven so as to expand or contract in a radial direction for the purpose of removing the blockage in the vessel.

Patent Document 2 discloses a catheter having a mesh-like self-expandable area. The catheter of Patent Document 2 includes a cover (a protective film) at the proximal end part of the self-expandable area, the cover serving as a funnel for guiding or directing a blood flow into a lumen of the catheter. The cover may be formed directly on the mesh by means of adhesive bonding, welding, coating or the like, or may be attached to the mesh with a mechanical fastening device.

Further, the catheter of Patent Document 2 may be used to capture a retrograde guide wire inserted from the opposite side of a blockage in a blood vessel.

Patent Document 1: Japanese Patent No. 3655920
Patent Document 2: Japanese Patent Application Laid-Open No. 2011-517424

However, the catheter of Patent Document 1 removes the blockage by scraping the blockage with two or more expanded wires. The blockage is then inserted into the catheter through a narrow distal end of the catheter. Thus, much of the blockage is left behind in the patient, resulting in a poor blockage-removing efficiency for the catheter.

When capturing a retrograde guide wire, the blockage-removing element of Patent Document 1 expands to raise the wires. While the blockage-removing element is expanded, the retrograde guide wire is inserted through the mesh of the blockage-removing element. Then, the blockage-removing element contracts so that the blockage-removing element constrains the retrograde guide wire with the two or more wires. Therefore, the retrograde guide wire may be inadvertently bent by the blockage-removing element. Accordingly, the catheter of Patent Document 1 may result in an increased risk of breakage.

The catheter of Patent Document 2 may not expand and/or contract the mesh smoothly because there is no degree of freedom in the movement of the cover relative to the mesh.

SUMMARY

Accordingly, an objective of the present disclosure is to provide a catheter with an increased efficiency for removing a blockage in a blood vessel, that prevents/reduces breakage of a retrograde guide wire, and that smoothly performs expansion and contraction of a mesh member having a protective film.

The disclosed embodiments include a catheter with a hollow shaft; a tubular mesh member joined to a distal end of the hollow shaft, the tubular mesh member comprising at least a first wire and a second wire interwoven so as to be configured to expand and contract in a radial direction; a distal tip joined to a distal end of the mesh member; a core wire joined to the distal tip, the core wire configured to control an expansion and contraction of the tubular mesh member; and a protective film covering at least a portion of an inner periphery of a proximal end part of the tubular mesh member, wherein the protective film is joined only to any one of either the first wire or the second wire.

The disclosed embodiments may guide a blockage in a blood vessel to the distal end of the catheter by virtue of the protective film, thus enhancing the efficiency for removing the blockage in the blood vessel. Further, a retrograde guide wire may enter into the mesh member and be directly and smoothly guided into the catheter by means of the guiding effect of the protective film. Therefore, the retrograde guide wire is not constrained by expansion and contraction operations of the mesh member, preventing the retrograde guide wire from breakage. Furthermore, the first wire and the second wire of the mesh member are not constrained by each other via the protective film. Therefore, the mesh member can be expanded and contracted smoothly.

The catheter according to the disclosed embodiments provides the following advantageous effects: improved efficiency for removing a blockage in a blood vessel; prevention/reduction of breakage of a retrograde guide wire; and smoothly performing expansion and contraction operations of the mesh member having the protective film.

BRIEF DESCRIPTION OF THE DRAWINGS

FIGS. 1A and 1B are schematic views illustrating a catheter according to disclosed embodiments.

FIGS. 7A and 7B are schematic views illustrating the catheter according to the disclosed embodiments.

DETAILED DESCRIPTION OF EMBODIMENTS

The present disclosure shall not be limited to the examples discussed herein, and modifications in design can be made appropriately. Note that in FIG. 1A, FIG. 2 and FIGS. 4 to 7A, the left side corresponds to the distal end side which is to be inserted into the body, and the right side corresponds to the proximal end side which is to be operated by an operator such as a physician.

Figures 1A, 1B:
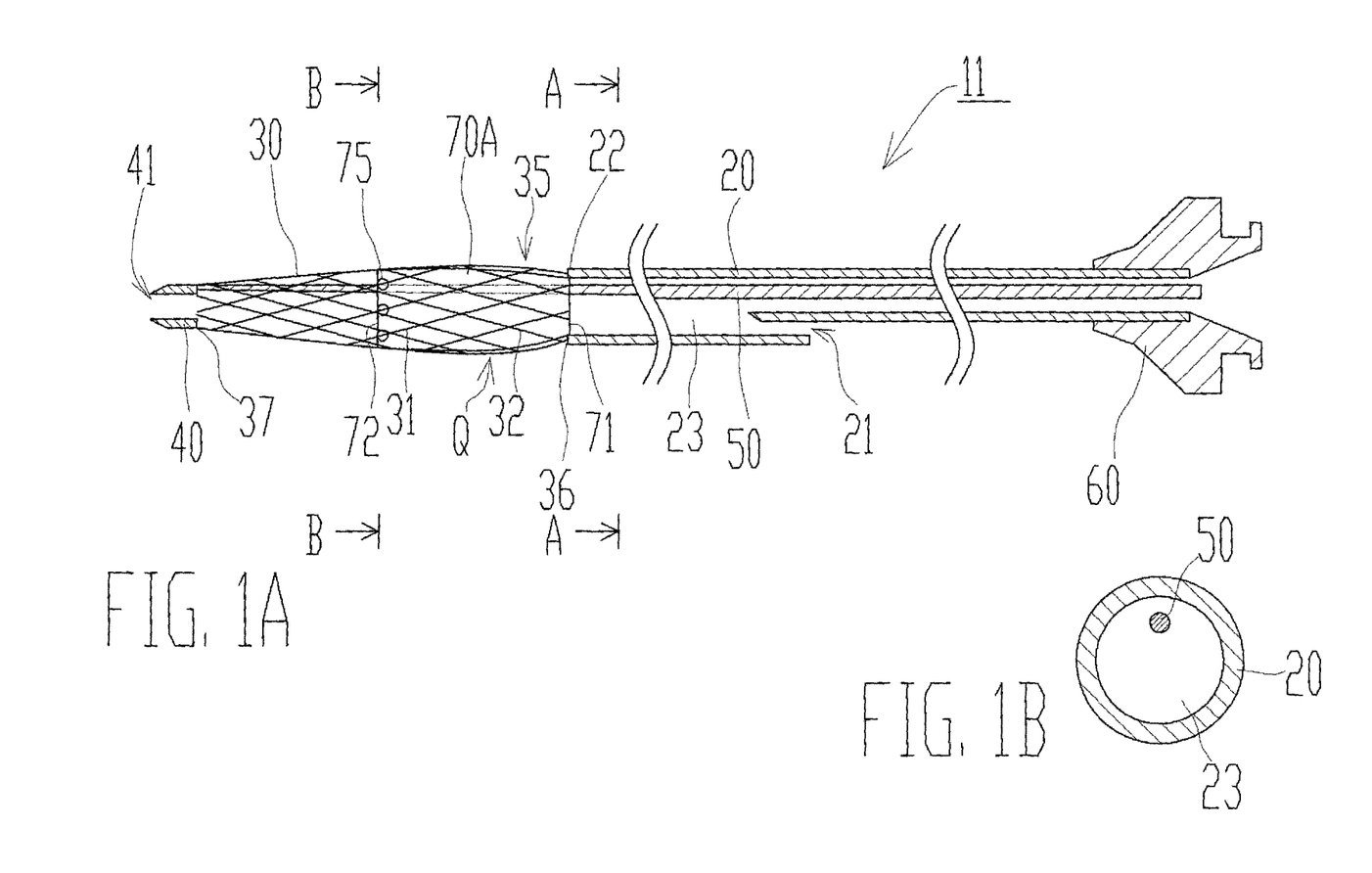
FIG. 1A is a schematic drawing of an overview.
FIG. 1B is a cross sectional view along A-A in FIG. 1A.

As shown in FIG. 1A, catheter 11 may be used for removing a blockage in a blood vessel. The catheter 11 includes a hollow shaft 20.

The hollow shaft 20 form a hollow tubular shape with an inner lumen 23. An RX port 21 opens toward a proximal end side of the hollow shaft 20 and is formed at a side wall between a distal end part of the hollow shaft 20 and a proximal end part of the hollow shaft 20.

The hollow shaft 20 may form a tube comprising, for example, a resin such as polyamide, polyamide elastomer, polyolefine, polyester or polyester elastomer. Further, a material of the proximal end side of the hollow tube 20 may be different from that of a distal end side of the hollow tube 20. For example, the proximal end side may comprise a superelastic alloy such as stainless steel (SUS 304) and a Ni—Ti alloy.

Moreover, a mesh member 30 may be joined to a distal end 22 of the hollow shaft 20. As shown in FIG. 1A, the mesh member 30 has a tubular shape in which a first wire 31 and a second wire 32 are interwoven together. A proximal end 36 of the mesh member 30 is joined to a distal end 22 of the hollow shaft 20 such that the mesh member 30 is substantially coaxially aligned with the hollow shaft 20.

The first wire 31 and the second wire 32 of the mesh member 30 may comprise, for example, a metal material such as stainless steel (SUS 304). In particular, an operator can accurately detect the location of the mesh member 30 during coronary angiography in a case where a radiopaque material (for example, tungsten or a Co—Cr alloy) is used in at least one of either the first wire 31 or the second wire 32.

Further, a distal tip 40 is joined to a distal end 37 of the mesh member 30. More specifically, the distal tip 40 has a tubular shape, and an opening 41 is formed at the distal end of the distal tip 40.

The distal tip 40 may be formed with a soft resin such as polyurethane or polyurethane elastomer.

Further, a core wire 50 is inserted through the inside of the hollow shaft 20 (through the lumen 23) such that a distal end of the core wire 50 is joined to a proximal end of the distal tip 40. The core wire 50 includes a tapered metal wire material having a circular cross section and a decreased diameter toward the distal end. As described below, the mesh member 30 can be expanded or contracted in a radial direction by controlling and operating the core wire 50 in an axial direction.

Additionally, a connector 60 is joined to the proximal end of the hollow shaft 20.

Furthermore, a thin flexible protective film 70A is arranged in a tube-like fashion at the inner periphery of the proximal end side 35 of the mesh member 30. As discussed further below, the protective film 70A covers the inner periphery of the proximal end side 35 of the mesh member 30. Note that for easier understanding, the hollow shaft 20, the distal tip 40, the connector 60, the core wire 50 disposed inside the hollow shaft 20, and the mesh member 30 are shown in a cross sectional view in FIGS. 1A and 2. Note that a portion of the core wire 50 inside the protective film 70A is shown with dashed lines.

The protective film 70A may be formed with, for example, a resin such as polyethylene, polyurethane, polyamide, polyamide elastomer, polyolefine, polyester or polyester elastomer, and a material that is used for a balloon of a common balloon catheter.

The protective film 70A covers the entire inner periphery of the proximal end side 35 of the mesh member 30. Further, a proximal end 71 of the protective film 70A extends proximally of the distal end 22 of the hollow shaft 20 such that the proximal end 71 is positioned inside the hollow shaft 20. Additionally, the proximal end 71 of the protective film 70A may not be joined to the distal end 22 of the hollow shaft 20.

Moreover, only the distal end part of the protective film 70A is joined to the mesh member 30 with an adhesive 75. Thus, as shown in FIG. 1A, a portion of the protective film 70A serves as a non joining portion Q that is not joined to the mesh member 30 at any position. This portion of the protective film 70A does not include the distal end part of the protective film 70A.

Figure 3:
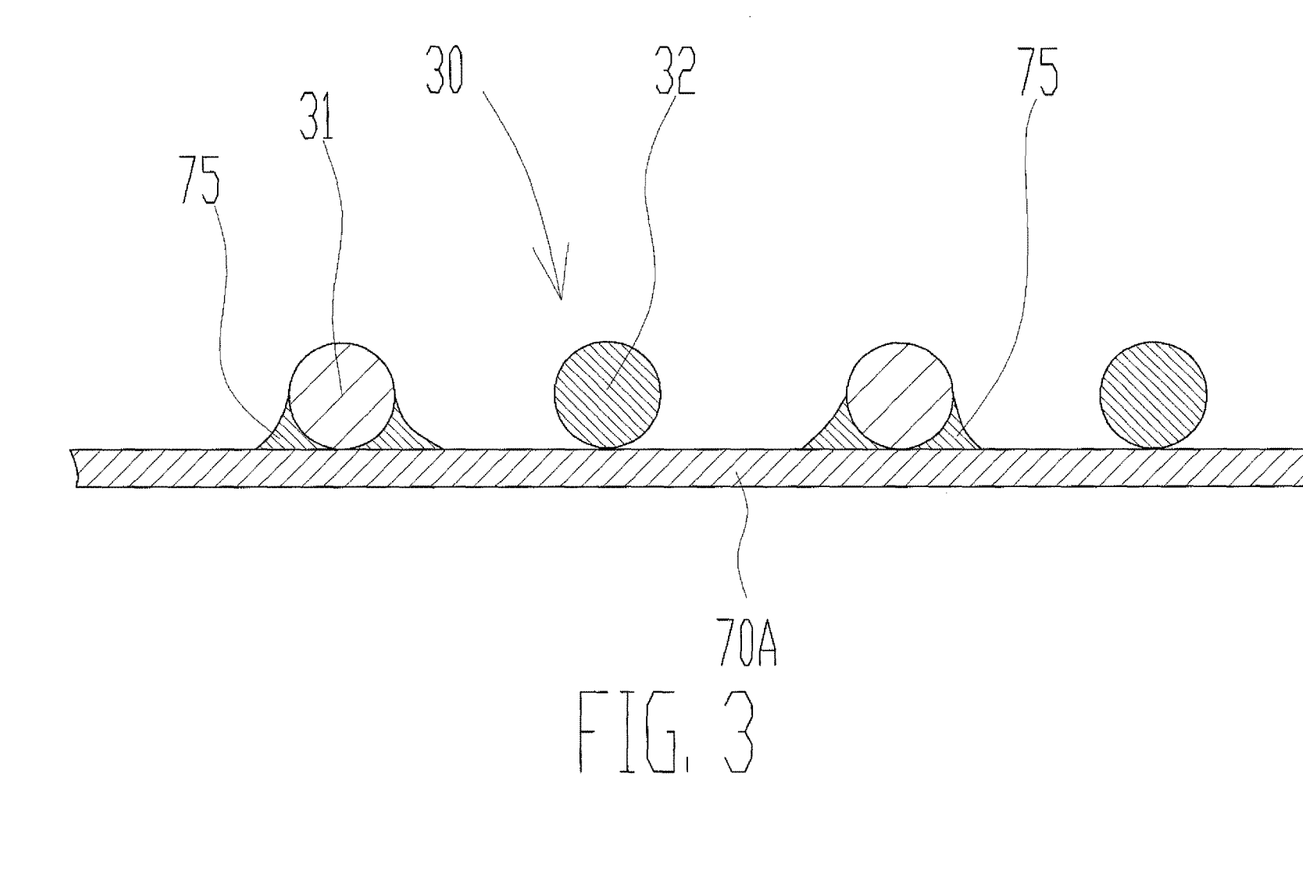
FIG. 3 is an enlarged partial cross-sectional view along B-B in FIG. 1A.

As shown in FIG. 3 in more detail, the distal end part of the protective film 70A is joined to the first wire 31 of the mesh member 30 with the adhesive 75. However, the distal end part of the protective film 70A is not joined to the second wire 32. Therefore, the protective film 70A and the second wire 32 may move independently relative to each other without being constrained by each other. The distal end part of the protective film 70A and the first wire 31 may only move together so that their movement is constrained by each other.

Figure 2:
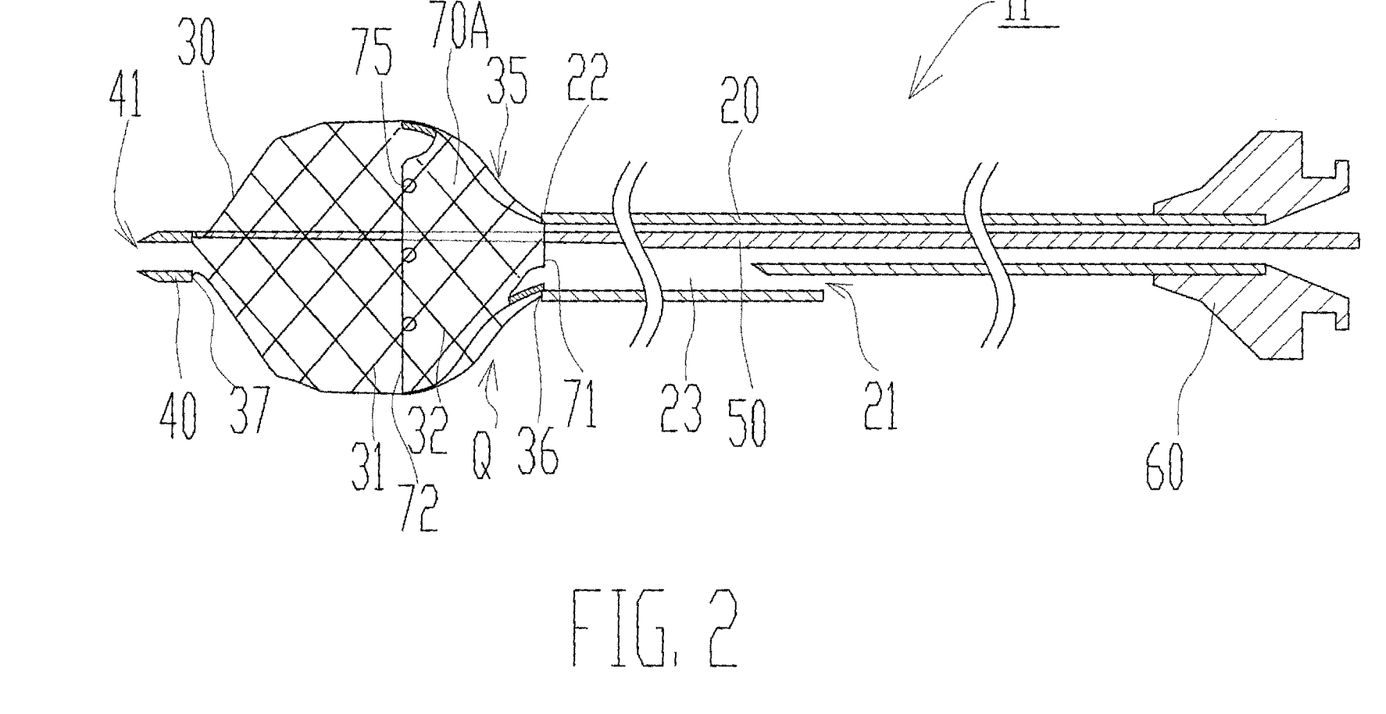
FIG. 2 is a schematic view illustrating the catheter according to the disclosed embodiments.

As shown in FIGS. 1A and 2, the diameter of the mesh member 30 expands or contracts when the core wire 50 is controlled and operated in an axial direction. For example, movement of the core wire 50 distally may contract the mesh member 30, and movement of the core wire 50 proximally may expand the mesh member 30. Expansion and contraction of the mesh member 30 changes the relative distance between the distal tip 40 and the hollow shaft 20.

The catheter 11 may be inserted into a blood vessel in a state when the diameter of the mesh member 30 is contracted, as shown in FIG. 1A. When the mesh member 30 reaches a predetermined position, such as a CTO site, the core wire 50 is operated so that the diameter of the mesh member 30 expands, as shown in FIG. 2. Note that a position where the diameter of the mesh member 30 increases and expands may appropriately be changed according to situations.

As the diameter of the mesh member 30 expands as described above, the distal end side of the protective film 70A follows the change in the state of the mesh member 30. Therefore, the diameter of the distal end side of the protective film 70A also increases so that the entire protective film 70A becomes funnel-like (FIG. 2).

When the diameter of the mesh member 30 is expanded as described above, a blockage in a blood vessel may be taken up into the hollow shaft 20 through the distal end 72 of the protective film 70A. For example, the blockage may flow between the first wire 31 and the second wire 32 in a portion of the mesh member 30 that is distal of the protective film 70A. The blockage may then flow into the hollow shaft 20. Alternatively, the blockage may flow through the opening 41 and into the hollow shaft 20.

Figure 4:
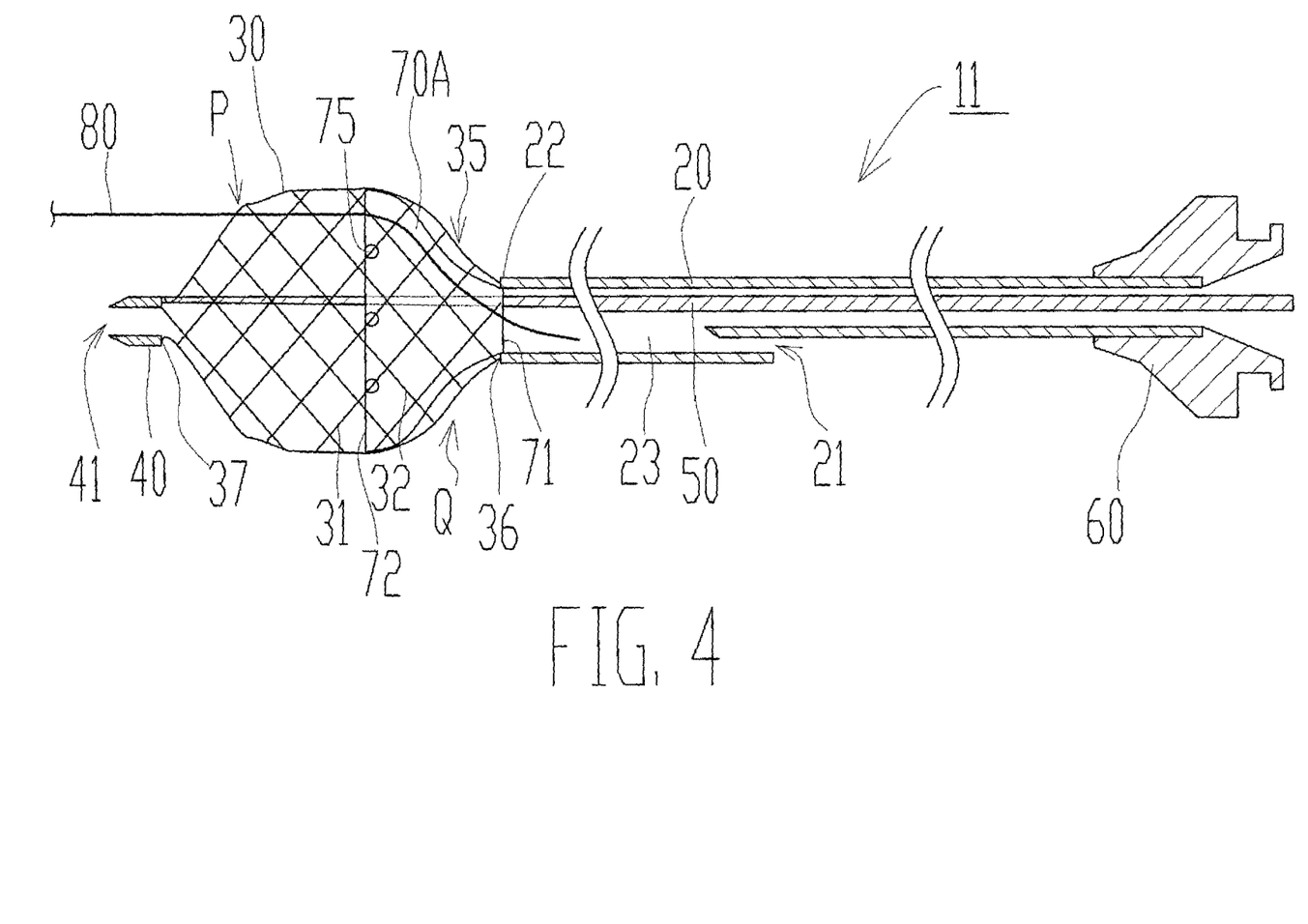
FIG. 4 is a schematic view illustrating the catheter according to the disclosed embodiments.

As shown in FIG. 4, the catheter 11 may be used with a retrograde guide wire 80. Thus, the retrograde guide wire 80 may be introduced through the distal end part of the mesh member 30 in a state when the mesh member 30 is expanded. The expanded mesh member 30 serves as an introducing portion P through which the retrograde guide wire 80 is to be introduced. The retrograde guide wire 80 is then inserted into the mesh member 30 through the introducing portion P, as shown in FIG. 4. Then, the retrograde guide wire 80 is guided into the hollow shaft 20 by virtue of the guiding effect of the protective film 70A, which has taken a funnel-like shape. Subsequently, the retrograde guide wire 80 may be removed from the patient through the lumen 23 and the RX port 21 of the hollow shaft 20. Therefore, the retrograde guide wire 80 that has been guided into the catheter 11 can be retrieved without breakage.

The distal end part of the protective film 70A has a high degree of freedom when the mesh member 30 is expanded because the distal end part of the protective film 70A is joined only to the first wire 31 of the mesh member 30. Thus, when the diameter of the mesh member 30 increases, the distal end part of the protective film 70A follows only the movement of the first wire 31 of the mesh member 30, and expands in a radial direction. This can avoid the problem that the first wire 31 and the second wire 32 are otherwise mutually restricted by the distal end part of the protective film 70A. Therefore, the mesh member 30 can be expanded or contracted smoothly.

Further, the proximal end part of the protective film 70A does not expand in a radial direction even when the mesh member 30 expands because the proximal end part of the protective film 70A is not joined to either the first wire 31 or the second wire 32. Therefore, when the mesh member 30 is expanded, the protective film 70A may easily be made into a funnel like shape with a diameter decreasing toward the direction of the proximal end. Moreover, the flexibility of the catheter 11 in a blood vessel is not impaired because the proximal end part of the protective film 70A is joined to neither the first wire 31 nor the second wire 32 of the mesh member 30, as described above.

The proximal end 71 of the protective film 70A extends to a position of the distal end 22 of the hollow shaft 20, as described above. Therefore, a blockage in a blood vessel and a retrograde guide wire 80 may each be guided smoothly into the hollow shaft 20 so that neither the blockage nor the retrograde guide wire 80 catches at the joining portion between the mesh member 30 and the hollow shaft 20. The proximal end 71 of the protective film 70A may extend proximally of the distal end 22 of the hollow shaft 20 so that the proximal end 71 extends into the lumen 23 of the hollow shaft 20.

Figure 5:
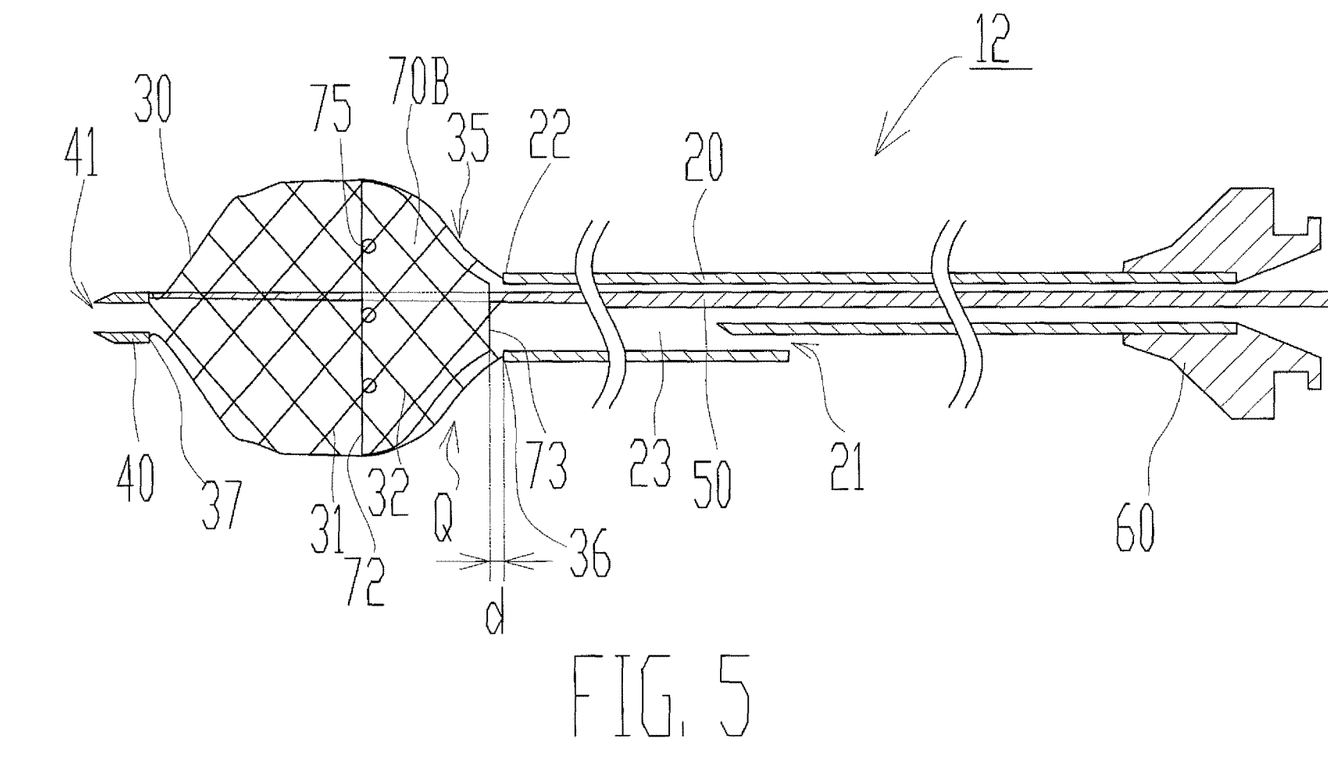
FIG. 5 is a schematic view illustrating the catheter according to the disclosed embodiments.

A catheter 12 according to disclosed embodiments will be described with reference to FIG. 5. Note that the same reference numbers are assigned to structures similar to those referenced above, and the descriptions thereof are omitted.

According to the catheter 12, a proximal end 73 of a protective film 70B is spaced from the distal end 22 of the hollow shaft 20 by a distance d. Therefore, the protective film 70B partially covers the inner periphery of the proximal end side of the mesh member 30. The proximal end 73 of the protective film 70B is not constrained by the hollow shaft 20. Therefore, the degree of freedom in expanding or contracting the protective film 70B is further improved, leading to even smoother operations of expanding or contracting the mesh member 30.

Figure 6:
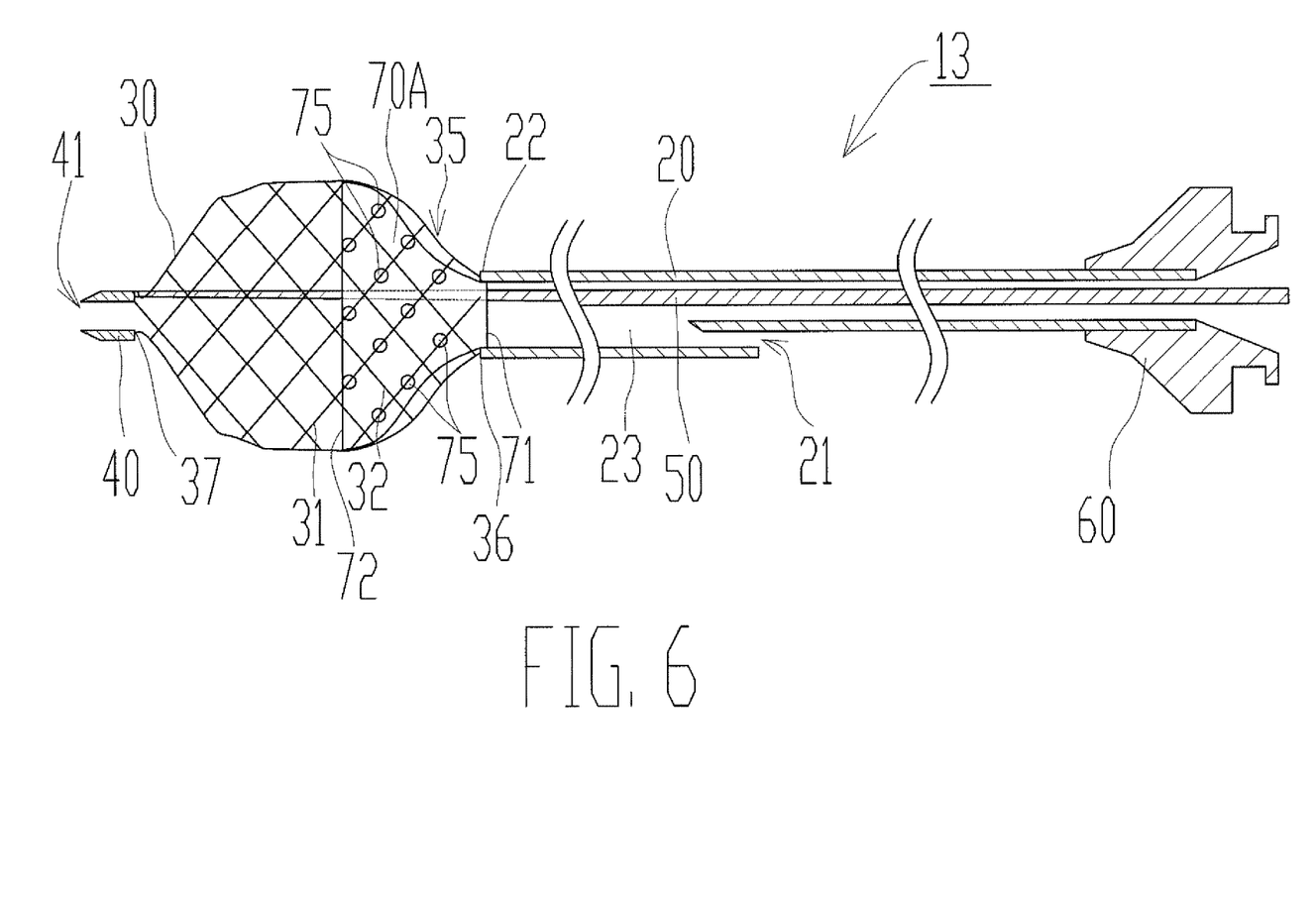
FIG. 6 is a schematic view illustrating the catheter according to the disclosed embodiments.

A catheter 13 according to disclosed embodiments will be described with reference to FIG. 6. Note that the same reference numbers are assigned to structures similar to those referenced above, and the descriptions thereof are omitted.

The protective film 70A of the catheter 13 is joined to the first wire 31 of the mesh member 30 from the distal end part through the proximal end part of the protective film 70A. Therefore, the catheter 13 does not include the aforementioned non-joining portion Q. The protective film 70A is joined only to the first wire 31 of the mesh member 30. Therefore, the mesh member 30 may be smoothly expanded or contracted. Furthermore, the protective film 70A is joined to the first wire 31 with the adhesive 75.

Figures 7A, 7B:
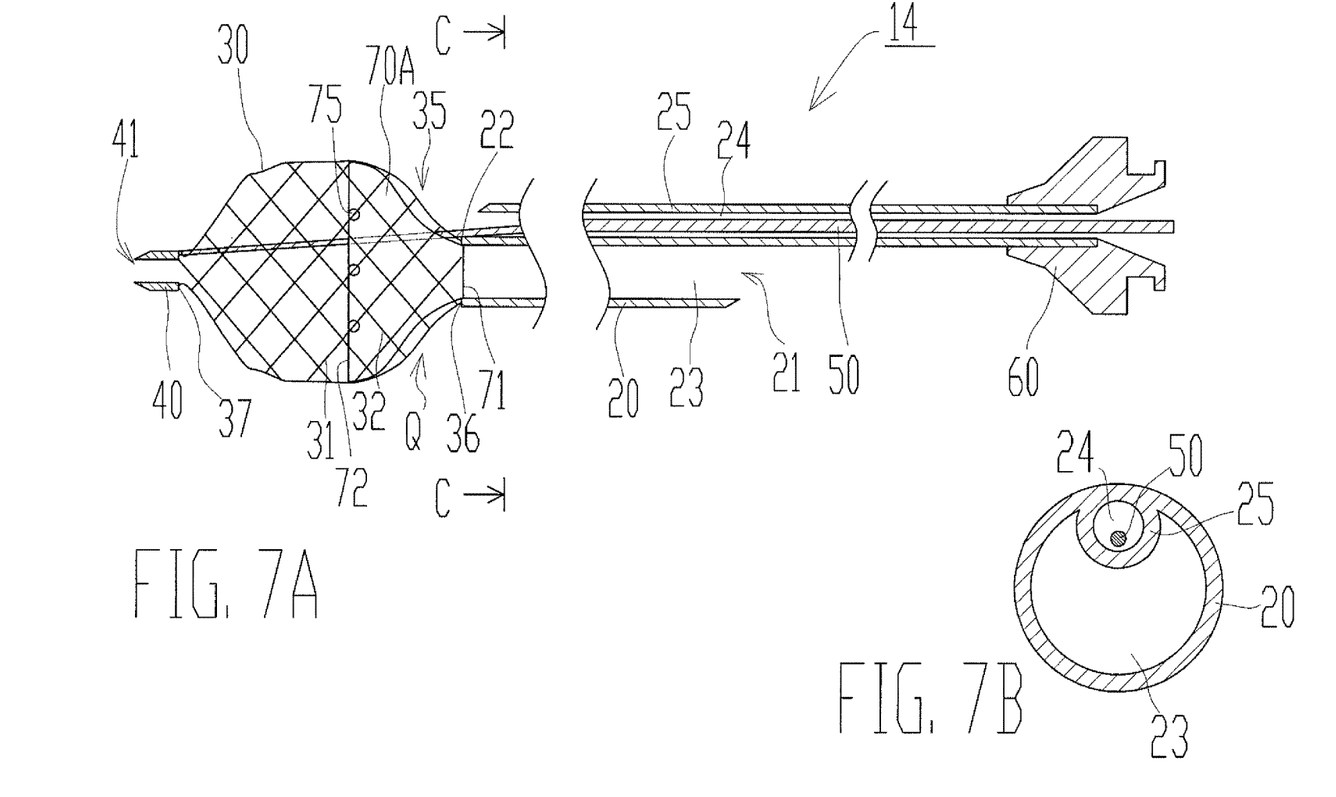
FIG. 7A is a schematic drawing of an overview.
FIG. 7B is a cross sectional view along C-C in FIG. 7A.

A catheter 14 according to disclosed embodiments will be described with reference to FIGS. 7A and 7B. Note that the same reference numbers are assigned to structures similar to those referenced above, and the descriptions thereof are omitted.

The catheter 14 has a so-called dual-lumen structure in which a second hollow shaft 25, distinct from the hollow shaft 20, is inserted into the hollow shaft 20, and the hollow shaft 20 and the second hollow shaft 25 are fused to each other. The lumen 23 is formed between the hollow shaft 20 and the second hollow shaft 25, and a second lumen 24, through which the core wire 50 is inserted, is formed inside the second hollow shaft 25. Unlike the previous disclosed embodiments, the core wire 50 is not inserted into the lumen 23 of the hollow shaft 20. Therefore, interference between the core wire 50 and the retrograde guide wire 80 may be avoided in the lumen 23 of the hollow shaft 20. Further, an operation of the core wire 50 in an axial direction is not blocked by the blockage in the lumen 23 so that the mesh member 30 can smoothly be expanded or contracted.

Note that modifications may appropriately be made to the disclosed embodiments. For example, the hollow shaft 20 may have a mono-layer structure, or may have a multi-layer structure with two or more layers.

Further, the mesh member 30 may include additional wires in addition to the first wire 31 and the second wire 32.

Moreover, the protective film 70A, 70B may be joined to the first wire 31 with other joining means than the adhesive 75. For example, the protective film 70A, 70B may be partially fused to the first wire 31.

Further, the protective film 70A, 70B may be joined only to the second wire 32 instead of the first wire 31. Note that in FIGS. 1A-7B, the protective film 70A, 70B and the first wire 31 are joined at a position off an intersection between the first wire 31 and the second wire 32, but the disclosure is not limited to this. The protective film 70A, 70B may be joined only to any one of either the first wire 31 or the second wire 32 at an intersection between the first wire 31 and the second wire 32.

Further, the protective film 70A, 70B may be configured with, for example, a mesh material that is finer than the mesh member 30 as long as it can guide a blockage in a blood vessel and the retrograde guide wire 80 into the hollow shaft 20.

Moreover, off course, a plurality of the protective films 70A, 70B may be arranged along the axial direction against the mesh member 30.

Note that, for the retrograde guide wire 80, those commonly used and publicly known can suitably be used.

What is claimed is:
1. A catheter comprising:
a hollow shaft;
a tubular mesh member joined to a distal end of the hollow shaft, the tubular mesh member comprising at least a first wire and a second wire interwoven so as to be configured to expand and contract in a radial direction, and the tubular mesh member including a proximal end part, a middle part, and a distal end part;
a distal tip joined to the distal end part of the mesh member;
a core wire joined to the distal tip, the core wire configured to control an expansion and contraction of the tubular mesh member; and
a protective film covering at least a portion of an inner periphery of the proximal end part of the tubular mesh member,
wherein:
a distal end of the protective film is joined only to any one of either the first wire or the second wire at the middle part of the tubular mesh member, and
a proximal end of the protective film is not joined to either the first wire or the second wire and is not joined to the distal end of the hollow shaft.

2. The catheter according to claim 1, wherein the proximal end of the protective film extends to a position of the distal end of the hollow shaft.

3. The catheter according to claim 2, wherein the protective film is configured to form a funnel-like shape with a diameter decreasing toward a direction of the proximal end of the protective film when the tubular mesh member is expanded.

4. The catheter according to claim 1, wherein the protective film is configured to form a funnel-like shape with a diameter decreasing toward a direction of the proximal end of the protective film when the tubular mesh member is expanded.

5. The catheter according to claim 1, wherein the proximal end of the protective film extends proximally of the distal end of the hollow shaft.

6. The catheter according to claim 1, wherein the protective film is joined only to any one of either the first wire or the second wire at only the distal end of the protective film.

7. The catheter according to claim 1, wherein the protective film is joined only to any one of either the first wire or the second wire between the distal of the protective film and the proximal end of the protective film.

8. The catheter according to claim 1, wherein the proximal end of the protective film is distal to the distal end of the hollow shaft, and a gap is provided between the proximal end of the protective film and the distal end of the hollow shaft.

9. A catheter comprising:
a hollow shaft;
a tubular mesh member joined to a distal end of the hollow shaft, the tubular mesh member comprising at least a first wire and a second wire interwoven so as to be configured to expand and contract in a radial direction;
a distal tip joined to a distal end of the mesh member;
a core wire joined to the distal tip, the core wire configured to control an expansion and contraction of the tubular mesh member; and
a protective film covering at least a portion of an inner periphery of a proximal end part of the tubular mesh member,
wherein:
the protective film is joined only to any one of either the first wire or the second wire and is joined to the tubular mesh member at a plurality of positions in a circumferential direction of the tubular mesh member, and
a proximal end of the protective film is not joined to either the first wire or the second wire and is not joined to the distal end of the hollow shaft.

10. A catheter comprising:
a hollow shaft;
a tubular mesh member joined to a distal end of the hollow shaft, the tubular mesh member comprising at least a first wire and a second wire interwoven so as to be configured to expand and contract in a radial direction;
a distal tip joined to a distal end of the mesh member;
a core wire joined to the distal tip, the core wire configured to control an expansion and contraction of the tubular mesh member; and
a protective film covering at least a portion of an inner periphery of a proximal end part of the tubular mesh member,
wherein:
the protective film is joined only to any one of either the first wire or the second wire and is joined to the tubular mesh member at a plurality of positions in a circumferential direction of the tubular mesh member in a state that a distal end of the protective film is positioned between the distal end and a proximal end of the tubular mesh member, and
a proximal end of the protective film is not joined to either the first wire or the second wire and is not joined to the distal end of the hollow shaft.

* * * * *